(12) United States Patent
Weber

(10) Patent No.: US 6,441,201 B1
(45) Date of Patent: Aug. 27, 2002

(54) METHOD FOR THE PREPARATION OF 5-CYANOPHTHALIDE

(75) Inventor: Beat Weber, Zofingen (CH)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/917,180

(22) Filed: Jul. 27, 2001

Related U.S. Application Data

(63) Continuation of application No. PCT/DK00/00032, filed on Jan. 26, 2000.

(30) Foreign Application Priority Data

Jan. 29, 1999 (DK) ........................................ 1999 00128

(51) Int. Cl.[7] ............................................ C07D 307/28
(52) U.S. Cl. ........................................................ 549/468
(58) Field of Search ........................................ 549/468

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 415/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 2001/0027256 A1 | 10/2001 | Petersen et al. | 549/462 |
| 2002/0004604 A1 | 1/2002 | Petersen et al. | 549/462 |
| 2002/0019546 A1 | 2/2002 | Petersen et al. | 549/307 |
| 2002/0025982 A1 | 2/2002 | Petersen et al. | 514/469 |
| 2002/0026062 A1 | 2/2002 | Petersen et al. | 549/467 |

FOREIGN PATENT DOCUMENTS

| | | | | |
|---|---|---|---|---|
| DK | WO 00/39112 | * | 6/2000 | |
| EP | 1 095 926 | | 5/2001 | ........... C07C/33/46 |
| WO | 9819511 A2 | | 5/1998 | |
| WO | 98/19512 | | 5/1998 | |
| WO | 9819513 A2 | | 5/1998 | |
| WO | 99/30548 | | 6/1999 | |
| WO | 00/11926 | | 3/2000 | |
| WO | 00/12044 | | 3/2000 | |
| WO | 00/13648 | | 3/2000 | |
| WO | 00/23431 | | 4/2000 | ......... C07D/307/87 |
| WO | 01/45483 | | 6/2001 | |
| WO | 01/47877 | | 7/2001 | |
| WO | 01/66536 | | 9/2001 | ......... C07D/307/87 |

OTHER PUBLICATIONS

U.S. patent application Ser. No. 09/830,109, filed Oct. 19, 1999 (International filing date).
U.S. patent application Ser. No. 09/891,874, filed Jun. 25, 2001.
U.S. patent application Ser. No. 09/692,653, filed Oct. 19, 2000.
U.S. patent application Ser. No. 09/977,920, filed Oct. 15, 2001.
U.S. patent application Ser. No. 10/012,054, filed Nov. 6, 2001.
U.S. patent application Ser. No. 10/012,025, filed Nov. 6, 2001.
U.S. patent application Ser. No. 10/035,005, filed Dec. 20, 2001.
U.S. patent application Ser. No. 10/046,126, filed Jan. 8, 2002.
Bigler, Allan et al., "Quantitative Structure–activity Relationships in a Series of Selective 5–HT uptake inhibitors," *Eur. J. Med. Chem.* 3:289–295 (1997).
Forney L., "Reaction of Terephthalic Acid with Formaldehyde in Sulfur Trioxide Media," *J. Org. Chem.* 35:1695–1696 (1970).
Dordor et al., "Reaction of Oxazolines with Phosphorus Oxychloride," *Tetrahedron Letters* 24:1437–1440 (1983).
Barton et al., *Comprehensive Organic Chemistry. The Synthesis and Reactions of Organic Compounds*, vol. 2, pp. 1024–1025.
Huber et al., "Preparation of Nitriles from Carboxylic Acids: A New, Synthetically Useful Example of the Smiles Rearrangement," *Tetrahedron* 54: 9281–9288 (1998).
"Phtalides substitués en 5," *Bull. Soc. Sci. Bretagne* 26: 35–43 (1951).
Levy et al., "Aminophthalide and Some Derivatives," *Chemistry Society. London Journal* 867–871 (1931).

* cited by examiner

*Primary Examiner*—T. A. Solola
*Assistant Examiner*—Joseph Murray
(74) *Attorney, Agent, or Firm*—Darby & Darby

(57) ABSTRACT

A method for the preparation of 5-cyanophthalide in which 5-carboxyphthalide is reacted with a dehydrating agent, such as thionylchloride, and a sulphonamide, in particular sulfamide. Cyanophthalide is prepared in high yields by a convenient procedure. 5-cyanophthalide is an intermediate used in the preparation of the antidepressant drug citalopram.

12 Claims, No Drawings

METHOD FOR THE PREPARATION OF 5-CYANOPHTHALIDE

This is a continuation of international application Ser. No. PCT/DK00/00032, filed Jan. 26, 2000, the entire disclosure of which is hereby incorporated by reference.

The present invention relates to a novel process for the preparation of 5-cyanophthalide which is an intermediate used for the manufacture of the well known antidepressant drug citalopram, 1-[3-(dimethylamino)propyl]-1-(4-fluorophenyl)-1,3-dihydro-5-isobenzofuran-carbonitrile.

BACKGROUND OF THE INVENTION

Citalopram is a well known antidepressant drug that has now been on the market for some years and has the following structure:

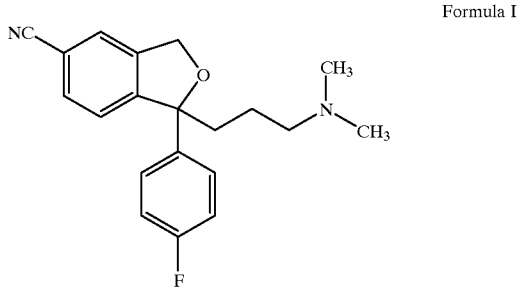

Formula I

It is a selective, centrally active serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75, 478–486.

Citalopram may be prepared by the process described in U.S. Pat. No. 4,650,884, according to which 5-cyanophthalide is subjected to two successive Grignard reactions, i.e. with 4-fluorophenyl magnesium halogenide and N,N-dimethylaminopropyl magnesium halogenide, respectively, and the resulting compound of the formula

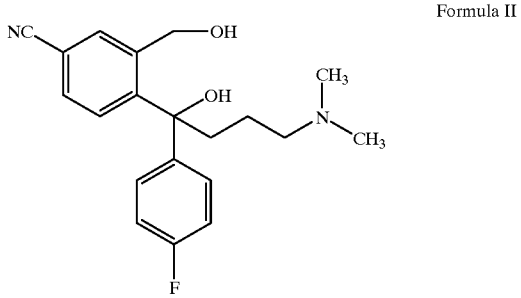

Formula II is subjected to a ring closure reaction by dehydration with strong acid.

Enantiomers of citalopram may be prepared by the method described in U.S. Pat. No. 4,943,590, i.e. by separating the enantiomers of the intermediate of Formula II and performing enantioselective ring closure in order to obtain the desired enantiomer.

Thus, 5-cyanophthalide is an important intermediate for the manufacture of citalopram and it is important to produce this material in an adequate quality, by a convenient process and in a cost-effective way.

A method for the preparation of 5-cyanophthalide has previously been described in *Bull. Soc. Sci. Bretagne,* 1951, 26, 35 and in Levy and Stephen, *J. Chem. Soc.*, 1931, 867. By this method, 5-aminophthalide is converted to the corresponding 5-cyanophthalide by diazotation followed by reaction with CuCN. 5-Aminophthalide was obtained from 4-aminophthalimide by a two step reduction procedure.

Synthesis of certain alkyl- and phenylnitriles from acid chlorides is described in *Tetrahedron Letters,* 1982, 23, 14, 1505–1508, and in *Tetrahedron,* 1998, 54, 9281.

Though a number of other methods failed, it has now been found that 5-cyanophthalide may be prepared in high yields by a convenient, cost-effective one-pot procedure from 5-carboxyphthalide.

DESCRIPTION OF THE INVENTION

Accordingly, the present invention provides a novel method for the preparation of 5-cyanophthalide

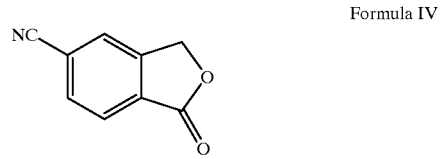

Formula IV comprising reaction of 5-carboxyphthalide

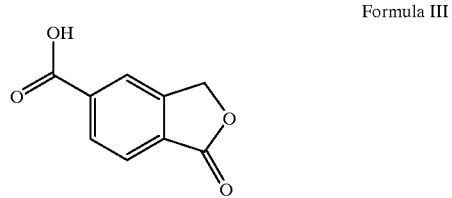

Formula III with a dehydrating agent and a sulfonamide of the formula $H_2N-SO_2-R$ (Formula V) wherein R is a) $NH_2$, $C_{1-6}$ alkyloxy, phenyloxy, b) phenyloxy substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino, or c) phenyl substituted with one or more electron withdrawing substituents in order to obtain 5-cyanophthalide.

Any suitable dehydrating agent may be used and the optimal agent may easily be determined by a person skilled in the art. Examples of suitable dehydrating agents are $SOCl_2$, $POCl_3$, $PCl_5$, $SOBr_2$, $POBr_3$, $PBr_5$, $SOI_2$, $POI_3$, $PI_5$ and oxalylchloride. Preferably a chloro-containing agent, most preferably $SOCl_2$, is used.

The term electron withdrawing substituent is intended to mean any substituent that is sufficiently electron withdrawing to allow the reaction to proceed, such as nitro, cyano, halogen, trifluoromethyl or aminosulfonyl. 3,5-Dinitrophenyl is an example of such a phenyl group substituted with electron withdrawing substituents.

In the method of the invention, the 5-carboxyphthalide reacts with the dehydration agent in order to form the corresponding 5-haloformyl derivative which then reacts with the sulfonamide of the formula V thereby forming the 5-cyanophthalide. During the latter reaction, a catalytic amount of an acid may be necessary. The 5-haloformyl derivative may, if desired, be isolated prior to further reaction. However, preferably the reaction is carried out as a one-pot procedure without isolation of the 5-haloformyl intermediate. Preferably the reaction proceeds via the 5-chloroformylphthalide.

The sulfonamide of Formula V used in the process is preferably sulfamide, i.e. a compound of Formula V wherein R is $NH_2$.

The reaction is carried out neat or in a suitable solvent, such as sulfolane or acetonitrile. Preferably, sulfolane is used as the solvent.

Thus, in a preferred embodiment of the invention, 5-carboxyphthalide is reacted with sulfamide in the presence of $SOCl_2$ in a sulfolane solution The reaction is carried out at elevated temperature. When sulfolane is used as the solvent, the reaction is preferably carried out at about 120–150° C.

5-Cyanophthalide may be isolated in a conventional way, e.g. by addition of water, filtration and subsequent washing of the crystals. Further purification may if desired be performed by recrystallisation.

Conveniently, 1.0 to 2.0 equivalents of sulfamide and dehydrating agent, respectively, are reacted with 1.0 equivalent 5-carboxyphthalide. Preferably, 1.0–1.2 equivalent sulfamide is used.

By the process of the invention, 5-cyanophthalide is obtained in high yields (>about 70%). The process is much more convenient than the known process and uses more convenient and cheaper reactants and conditions. Furthermore, due to the fact that the process is a one-pot procedure the capacity is substantially increased and accordingly the costs are substantially reduced.

The 5-carboxyphthalide used as a starting material may be obtained by the methods described in U.S. Pat. No. 3,607,884 or German patent No. 2630927, i.e. by reacting a concentrated solution of terephthalic acid with formaldehyde in liquid $SO_3$ or by electrochemical hydrogenation of trimellithic acid.

EXAMPLES

The invention is further illustrated by the following examples.

Example 1

5-Cyanophthalid

5-Carboxyphthalid (50 g, 0.28 mole) and sulfamide (31 g, 0.32 mole) were suspended in sulfolane (150 mL). Thionylchloride (41 g, 0.34 mole) was added and the temperature was raised to 130–140° C. for 2 hours. At about 90° C., gas evolution took place. The mixture was allowed to cool to 90° C. and water (150 mL) was added. The temperature was held at 85–90° C. for 15 min and then the solution was cooled to 35° C. The crystals were filtered off and washed with water (250 mL). The title compound was crystallised from acetic acid.Yield: 34.5 g, 77%. DSC onset: 203° C. Purity: 98.5% (hplc, peak area). $^1H$ NMR (DMSO-$d_6$, 500 MHz): 5.48 (2H, s), 8.03 (2H, s), 8.22 (1H, s). $^{13}C$ NMR (DMSO-$d_6$, 125 MHz): 70.0, 116.1, 188.0, 126.0, 127.5, 129.0, 132.8, 147.7, 169.3.

Example 2

5-Cyanophthalid

Wet 5-carboxyphthalid (14 kg, approx. 6.3 kg dry, 35 mole) was suspended in sulfolane (23.5 kg). The water was removed by azeotropic distillation with toluene. Sulfamide (3.9 kg, 41 mole) and thionyl chloride (5.8 kg, 48 mole were added and the temperature was raised to 135–140° C. for 5 hours. At about 90° C. gas evolution took place. The mixture was allowed to cool to 90° C. and water (21.3 kg) was added. The temperature was held at 85–90° C. for 15 min and then the solution was cooled to 35° C. The crystals were filtered off and washed with water (14.2 kg). The title compound was crystallised from acetic acid. Yield: 3.8 kg, 68%. Purity: 99.5% (hplc, peak area).

Example 3

5-Cyanophthalid

5-Chlorocarbonylphthalid (24.3 g, 0.124 mole) was dissolved in sulfolane (51 g). Sulfamide (13.8 g 0.144 mole) was added and the temperature was raised to 135° C. for 3 hours. At about 90° C., gas evolution took place. The mixture was allowed to cool and water (100 g) was added. The temperature was held at 85–90° C. for 5 min and then the solution was cooled to 60° C. The crystals were filtered off and washed with water (60 g) and acetic acid (30 g). Then the title compound was dried in vacuo. Yield: 19 g, 96%. Purity: 98.2% (hplc, peak area).

What is claimed is:

1. A method for the preparation of 5-cyanophthalide

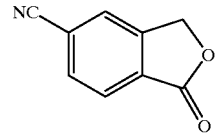

Formula IV comprising reaction of 5-carboxyphthalide

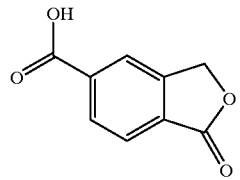

Formula III with a dehydrating agent and a sulfonamide of the formula $H_2N-SO_2-R$ (Formula V) wherein R is a) $NH_2$, $C_{1-6}$ alkyloxy, phenyloxy;

b) phenyloxy substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino; or c) phenyl substituted with one or more electron withdrawing substituents.

2. The method of claim 1 wherein the dehydrating agent is selected from the group consisting of $SOCl_2$, $POCl_3$, $PCl_5$, $SOBr_2$, $POBr_3$, $PBr_5$, $SOI_2$, $POI_3$, $OI_5$ or oxalylchloride.

3. The method of claim 2 wherein the dehydrating agent is selected from the group consisting of $SOCl_2$, $POCl_3$ or $PCl_5$.

4. The method of claim 3 wherein the dehydrating agent is $SOCl_2$.

5. The method of any of claims 1–3 wherein the sulfonamide used is a compound of Formula V wherein R is $NH_2$.

6. The method of any of claims 1–3 wherein the reaction is carried out without isolation of the 5-haloformylphthalide intermediate.

7. The method of any of claims 1–3 wherein the reaction is carried out neat.

8. The method of claim 1 wherein the reaction is carried out in sulfolane or acetonitrile.

9. The method of claim 8 wherein the reaction is carried out in sulfolane.

10. The method of claim 6 wherein 5-carboxyphthalide is reacted with sulfamide in the presence of $SOCl_2$ in a sulfolane solution.

11. The method of any of claims 1–3 wherein the 5-haloformylphthalide intermediate resulting from the reaction of 5-carboxyphthalide with dehydrating agent is isolated and then reacted with the sulfonamide.

12. The method of claim 11 wherein the reaction is carried out in sulfolane.

\* \* \* \* \*